United States Patent
Herwig et al.

(10) Patent No.: US 6,828,449 B2
(45) Date of Patent: Dec. 7, 2004

(54) USE OF A SETTLING ACCELERATOR IN EPOXIDATION

(75) Inventors: Juergen Herwig, Huenxe (DE); Martin Roos, Haltern am See (DE); Georg Oenbrink, Duelmen (DE); Bernd Guenzel, Haltern am See (DE); Joerg Lohmar, Dortmund (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/681,282

(22) Filed: Oct. 9, 2003

(65) Prior Publication Data

US 2004/0073051 A1 Apr. 15, 2004

(30) Foreign Application Priority Data

Oct. 11, 2002 (DE) .......................................... 102 47 496

(51) Int. Cl.$^7$ ............................................. C07D 301/03
(52) U.S. Cl. ....................................... 549/523; 549/518
(58) Field of Search .................................. 549/518, 523

(56) References Cited

FOREIGN PATENT DOCUMENTS

| DE | 30 27 349 | 2/1981 |
|---|---|---|
| EP | 0 987 259 | 3/2000 |
| EP | 1 167 334 | 1/2002 |

OTHER PUBLICATIONS

W. A. Herrmann, et al., Angew. Chem. vol. 103, No. 12, pp. 1706–1709, "Methyltrioxorhenium Als Katalysator Für Die Olefin–Oxidation", 1991.

M. Henschke, VDI–Verlag, No. 379, p. 1–2, "Dimensionierung Liegender Fluessig–Fluessig–Abscheider Anhand Diskontinuierlicher Absetzversuche", 1995.

*Primary Examiner*—Amelia A. Owens
(74) *Attorney, Agent, or Firm*—Oblon, Spivak, McClelland, Maier & Neustadt, P.C.

(57) ABSTRACT

Settling times of a catalyst in the epoxidation of a cyclic, at least monounsaturated alkene are improved by a method, comprising epoxidizing a cyclic, at least monounsaturated alkene having from 8 to 20 carbon atoms in the ring in a reaction medium containing an oxidant and a catalyst system comprising at least one metal of Groups 4, 5 and 6 of the Periodic Table of the Elements, phosphoric acid and a phase transfer catalyst and a cyclic alkane having from 8 to 20 carbon atoms in the ring, which corresponds to the alkene reactant, as settling accelerator in the epoxidation reaction.

17 Claims, 2 Drawing Sheets

USE OF A SETTLING ACCELERATOR IN EPOXIDATION

BACKGROUND OF THE INVENTION

1. Field of the Invention

The present invention relates to a novel settling accelerator for the epoxidation of a cyclic, at least monounsaturated alkene.

2. Description of the Background

Numerous processes for the epoxidation of alkenes are known and it is possible to use a wide range of different reaction or catalyst systems. The epoxidation of alkenes in a homogeneous, liquid phase using organic hydroperoxides in the presence of catalysts based on molybdenum, tungsten or vanadium is carried out industrially. However, epoxide production is accompanied by formation of equivalent or even greater amounts of the alcohol corresponding to the hydroperoxide, and the need to utilize or recirculate this alcohol greatly restricts industrial use of this process. For this reason, alternative processes for the more direct oxidation (epoxidation) of alkenes are being developed to an increasing extent.

One such process is epoxidation by means of molecular oxygen using silver catalysts. However, this process has only been able to be employed successfully for ethene and has not been able to be applied analogously to the epoxidation of other alkenes of the interest (for example propene).

Another process for direct oxidation of alkenes to epoxides is reaction with hydrogen peroxide. The process has been proposed for various epoxidation reactions because of, in particular, the positive aspect of the use of the oxidant in significantly reducing environmental pollution. Since the activity of hydrogen peroxide toward alkenes is only low, sometimes even completely absent, it is necessary to use activating agents, usually organic acids such as formic acid, acetic acid, etc., in organic solvents to facilitate the oxidation reaction. The acids form peracids in the reaction medium, which represent the actual reactive epoxidation agent, in situ. These processes, too, do not appear to be particularly successful, because it is difficult to obtain the peracids and because of the instability of the epoxides in acidic media, as a result of which varying convenient process conditions are necessary.

Still another method is the oxidation of alkenes by reaction with highly concentrated hydrogen peroxide in a homogeneous, i.e. exclusively organic, liquid phase in the presence of soluble catalyst systems based on elements of Groups 4, 5 and 6 of the Periodic Table (Ti, V, Mo, W) in combination with elements selected from the group consisting of Pb, Sn, As, Sb, Bi, Hg, and the like. Here too, the results of the process do not permit implementation as an industrial process. This is firstly because the reaction proceeds slowly, and secondly the preparation of the catalyst systems, which generally consist of very complicated organic metal compounds and additionally have to be soluble in the organic reaction medium, is complicated and expensive. Furthermore, the use of highly concentrated hydrogen peroxide (>70%) involves considerable safety risks which cannot easily be overcome in an economical manner.

These processes of the prior art clearly show that the oxidation of alkenes by means of hydrogen peroxide is self-contradictory because the best working conditions in respect of the catalyst system and hydrogen peroxide involve an aqueous, acidic medium while the factors of the oxidation reaction itself and the stability of the epoxide are favored in a neutral organic medium. For this reason, further processes for the epoxidation of alkenes using hydrogen peroxide have been developed, in which either an improved catalyst system based on $TiO_2/SiO_2$ in an aqueous phase with addition of primary or secondary alcohols (see EP 0 987 259 A1) or a two phase system containing a catalyst comprising tungstic acid, a quaternary ammonium salt and a phosphorous compound (for example DE 30 27 349) is used.

In the case of alkenes whose epoxides are not hydrolysis-labile and in which the olefinic double bond is not sterically hindered (e.g. cyclic at least monounsaturated alkenes), the known epoxidation using hydrogen peroxide and a tungsten catalyst is the most economical alternative.

For the epoxidation reaction by means of hydrogen peroxide to proceed sufficiently quickly, a phase transfer catalyst (for example, Aliquat® 336) is usually used in the case of very lipophilic alkenes (for example cyclododecene) (Angew. Chem. (1991), 103(12), 1706–9). However, the desired strong acceleration of the epoxidation by means of the phase transfer catalyst leads to the phases being significantly more difficult to separate after the reaction, because of emulsion formation; the corresponding settling times increase greatly. In addition, the organic phase usually remains very turbid after the separation. To achieve virtually complete phase separation, it is necessary to use either phase separators having a very large volume or suitable centrifuges.

The increased settling times in this process greatly reduce its attractiveness for continuous, industrial-scale use. In particular, the process can usually not be implemented at all in existing plants because of space problems caused by the need for larger phase separators. The use of centrifuges is of little interest in view of the power costs and the maintenance requirement required by moving parts.

It can be said quite generally that settling times of less than 2 minutes are industrially desirable. If, on the other hand, the settling times are more than 4 minutes, an industrial-scale continuous process is difficult to operate economically.

DE 30 27 349 describes a process for the epoxidation of alkenes using hydrogen peroxide, a tungsten compound, a phosphorus compound and a phase transfer catalyst. In this process, solvents such as alkanes or cycloalkanes are absolutely necessary. These solvents are always added to the reaction mixture in large amounts and generally serve either to dissolve a solid material and thus allow it to react, or to improve the reaction conditions, for example to achieve better heat removal.

However, the dilution of starting materials with non-reactive substances such as solvents is undesirable since, firstly, the dilution leads to a reduction in the space-time yield and, secondly, a further separation operation is necessary after the reaction.

SUMMARY OF THE INVENTION

Accordingly, one object of the present invention is to provide a settling accelerator, i.e. a compound, which leads to industrially acceptable settling times of the heterogeneous catalyst-containing reaction mixture in the epoxidation of alkenes, which ensures a sufficiently high space-time yield of epoxide, so that this process using the settling accelerator makes it possible for such epoxides to be prepared on an industrial scale.

Briefly, this object and other objects of the present invention as hereinafter will become more readily apparent can be attained by a method of improving settling times of catalyst in the epoxidation of a cyclic, at least monounsaturated alkene, comprising:

epoxidizing a cyclic, at least monounsaturated alkene having from 8 to 20 carbon atoms in the ring in a reaction medium containing an oxidant and a catalyst system comprising at least one metal of Groups 4, 5 and 6 of the Periodic Table of the Elements, phosphoric acid and a phase transfer catalyst and a cyclic alkane having from 8 to 20 carbon atoms in the ring, which corresponds to the alkene reactant, as settling accelerator in the epoxidation reaction.

BRIEF DESCRIPTION OF THE DRAWINGS

A greater understanding of the invention in its various embodiments can be ascertained from a consideration of the several drawings of the application, wherein.

DETAILED DESCRIPTION OF THE PREFERRED EMBODIMENTS

Figure 1:
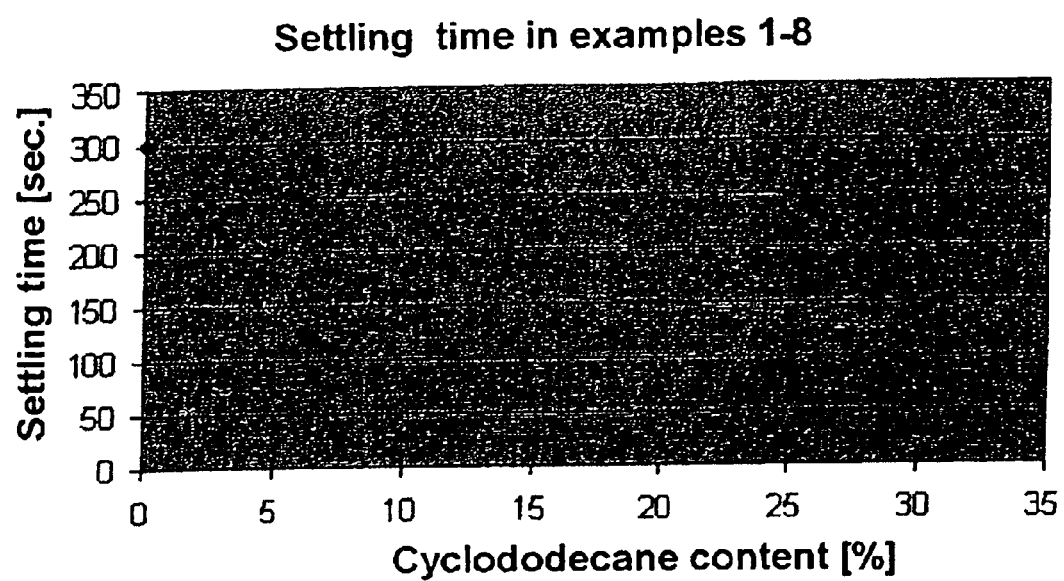
FIG. 1 is a graph of the settling times obtained in the experiments of Examples 1–8.

In a preferred embodiment of the invention, the settling accelerator of the invention is added to the reaction mixture in an amount of at least 1% by weight, particularly preferably at least 2.5% by weight.

Throughout the application, the expression "% by weight" means the proportion by weight expressed as a percentage of each component, based on the epoxide.

The result achieved in the invention is surprising which is that the presence of the alkane corresponding to the olefin reactant leads, even in small amounts, to a considerable acceleration of the settling times and thus to an overall more economical process.

In contrast to the epoxidation processes of the prior art, which use a phase transfer catalyst, the use in the invention of the settling accelerator leads to settling times of the heterogeneous mixture of catalyst and product obtained at the end of the oxidation reaction of less than two minutes.

For the purposes of the present invention, the term "settling time" is the time after which the phases of the reaction medium have completely separated. Phase separation is, by way of definition, regarded as complete when the last droplet layer covers only half the phase boundary and the other half can be seen to be a clear interface free of dispersion droplets (cf.: "Dimensionierung liegender Flüssig-Flüssig-Abscheider anhand diskontinuierlicher Absetzversuche", Dipl. Ing. Martin Henschke, VDI-Verlag, Düsseldorf, 1995).

As stated here and hereinafter, the term "corresponding alkane" refers to the compound which is identical to the compound which would be obtained by complete hydrogenation of the alkene used as the starting reactant.

Even if the upper limit of the corresponding alkane is itself not critical for the reduction of the settling time, preference is given to using only a small amount of the corresponding alkane, in general not more than 10% by weight, to achieve the object of the invention, in particular so as to ensure an acceptable space-time yield. In the present invention, the corresponding alkane does not function as solvent.

In a particularly preferred embodiment of the present invention, the amounts of the corresponding alkane employed in the reaction medium are, however, so small that the space-time yield of the epoxidation reaction is reduced only insignificantly.

A further, likewise preferred aspect of the invention is that the epoxidation reaction is conducted continuously.

Suitable oxidants include all those compounds known to those skilled in the art to be useful in the epoxidation reaction, in particular peroxo compounds. Particular preference is given to hydrogen peroxide as oxidant.

If a phase transfer catalyst is necessary to improve the reaction conditions of the oxidation reaction, the use or presence of a catalyst system which is or comprises at least one metal of Groups 4, 5 and 6 of the Periodic Table of the Elements is preferred. Further constituents of the catalyst system include phosphoric acid and at least one quaternary ammonium salt or a tertiary amine. However, mixtures of these catalyst systems can also be used depending on the desired reaction conditions. When using such a catalyst system, preference is given to the addition of phosphoric acid and at least one quaternary ammonium salt to the reaction mixture to achieve optimum reaction conditions.

The preferred catalyst for the epoxidation is a metal of Group 4, 5 or 6 of the Periodic Table which can be used in metallic form or in the form of a complex in which the metal is in the oxidation state zero or in which the metal has a variable oxidation state. Particular preference is given to molybdenum, tungsten, vanadium, chromium and titanium.

Among the inorganic derivatives of these elements, it is possible to use the oxides, the mixed oxides, the hydroxides, oxo acids, heteropolyacids, their salts and esters, the salts derived from hydrogen acids and from inorganic oxo acids and organic carboxylic or sulfonic acids having not more than 20 carbon atoms whose anions are stable under the reaction conditions.

Suitable examples of appropriate catalysts include molybdenum, tungsten, chromium, vanadium, titanium, the carbonylated metals $Mo(CO)_6$, $W(CO)_6$, the oxides $MoO_2$, $Mo_2O_5$, $Mo_2O_3$, $MoO_3$, $WO_2$, $W_2O_5$, $WO_6$, $CrO_2$, $Cr_2O_3$, $CrO_3$, $VO_2$, $V_2O_5$, $ZrO_2$, $TiO$, $TiO_2$, $Ti_2O_3$, $NbO_2$, $Nb_2O_3$, $Nb_2O_5$, the sulfides $MoS_2$, $MoS_3$, $MoS_4$, $Mo_2S_3$, $Mo_2S_5$, the oxychlorides of molybdenum, tungsten, chromium, vanadium, zirconium, titanium, the fluorides, chlorides, bromides, iodides, nitrates, sulfates, phosphates, pyrophosphates, polyphosphates, borates, carbonates, formates, octanoates, dodecanoates, naphthenates, stearates, oxalates, succinates, glutarates, adipates, benzoates, phthalates, benzenesulfonates of molybdenum, tungsten, titanium, chromium, zirconium, vanadium, complexes such as the acetylacetonates and phthalocyanines; the molybdic, tungstic, vanadic and chromic acids, the corresponding heteropolyacids such as phosphomolybdic, phosphotungstic, arsenomolybdic, arsenotungstic acids and also all alkali metal or alkaline earth metal salts of these acids.

In a particularly preferred embodiment of the present invention, a tungsten catalyst with addition of phosphoric acid is used. The tungsten compound is preferably used in a concentration ranging from 0.01 to 0.5 mol %, based on the alkene. The amount of phosphoric acid employed usually ranges from 0.1 to 5 mol %, based on the molar amount of tungsten used.

Suitable quaternary ammonium salts have the formula

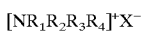

wherein $R_x$, $R_2$, $R_3$ and $R_4$ are, independently of one another, linear or branched alkyl chains having from 1 to 20 carbon atoms or aryl groups having from 6 to 10 carbon atoms. The alkyl or aryl groups may be substituted by organic groups or atoms such as halogens. X is a counterion for the ammonium ion, for example, chloride, bromide, fluoride, iodide, hydrogensulfate, acetate, propionate or formate.

The tertiary amines have 3 alkyl radicals which may be identical or different and have a total of at least 18 carbon atoms.

In general, the catalyst employed preferably is a homogeneous catalyst. However, it is also possible to use a heterogeneous catalyst in which the catalytically active constituents have been applied to a support material, for example, aluminum oxide, silicon dioxide, aluminum silicate, zeolites or suitable polymers, in a manner known per se.

The best results in the epoxidation described have been obtained using a catalyst as described in DE 30 27 349. This catalyst comprises a first component comprising at least one element or at least one inorganic, organic or organometallic derivative of an element selected from the group consisting of W, Mo and V, preferably W, which can be converted in situ and under the reaction conditions into a catalytically active compound.

A particularly useful system comprises 0.2 mol % of sodium tungstate based on cycloalkene, 0.2 mol % of phase transfer catalyst trioctylmethylammonium chloride based on cycloalkene, 0.1 mol % of phosphoric acid based on cycloalkene and that amount of sulfuric acid which brings the pH of the reaction medium to 3.

In another, likewise preferred embodiment, the reaction mixture comprises at least two liquid phases. One of these phases is an aqueous phase in which the hydrogen peroxide is dissolved. This eliminates the use of polar solvents and the associated decrease in the space-time yield and also the increased difficulty of separation.

In still another preferred embodiment, the pH should be kept constant during the reaction. This can be achieved by means of automatic pH regulation. A pH range which has been found useful for the purposes of the present invention ranges from 2 to 6. The reaction is particularly preferably conducted at a pH ranging from 2.5 to 4.

Suitable cyclic, at least monounsaturated alkene reactants include all suitable such compounds.

These alkenes may, if desired, be substituted by functional groups which are stable in the reaction medium, for example, hydroxy, chloro, fluoro, bromo, iodo, nitro, alkoxy, amino, carbonyl, acid, ester, amide or nitrile radicals.

However, they can also be multiply unsaturated, for example, dienes and trienes in conjugated or nonconjugated form.

The settling accelerator of the present invention is particularly preferred for the epoxidation of cyclic, at least monounsaturated alkenes which have from 8 to 20 carbon atoms in the ring. Compounds of this type include, in particular, cyclooctene, cyclooctadiene, cyclodecene, cyclododecadiene, cyclododecatriene, dicyclopentadiene and cyclododecene. Alkenes of this type which have more than nine carbon atoms in particular can be prepared in a significantly better space-time yield compared to the processes of the prior art. Very particular preference is given to the use of cyclododecene for preparing the corresponding cyclic epoxyalkanes which is 1,2 epoxycyclododecane.

For the purposes of the present invention, the alkane corresponding to the cyclic, at least monounsaturated alkene used is the cyclic, saturated organic compound having the same number of carbon atoms. The corresponding compounds are then selected, for example, from the group consisting of cyclooctane, cyclododecane and dicyclopentane.

The continuous process of the invention can be conducted in one or more reactors. An example is a cascade-like reaction employing a plurality of stages is described in EP 1 167 334 A2. In this disclosure, the reaction mixture is introduced into the first reaction zone and then passes through a plurality of downstream reaction zones until the product-containing mixture is finally discharged from the last reaction zone. The individual reaction zones may be present in different reactors or be integrated into one reactor.

The settling accelerator is particularly preferably used in epoxidation processes in which a phase transfer catalyst is also used and in which the starting mixture of alkene and the corresponding alkane are introduced together with the quaternary ammonium salt into a first reactor. Hydrogen peroxide containing phosphoric acid and the tungsten-based catalyst described in DE 30 27 349 is metered into this reactor in a molar amount corresponding to that of the alkene. The amount of hydrogen peroxide may be 20% above or below this amount. After a particular fill level corresponding to a particular residence time has been achieved in the first reactor, the solution is conveyed continuously either via an overflow or via a pump into a further reactor. A small amount of hydrogen peroxide without catalyst and phosphoric acid may, if desired, be fed into this second reactor. After a particular fill level corresponding to a particular residence time has been achieved in the second reactor, the solution is passed continuously either via an overflow or via a pump into a further reactor. A small amount of hydrogen peroxide without catalyst and phosphoric acid may, if desired, be fed into this third reactor. This form of reactor cascade can have from 2 to 8 stages. These stages can also be integrated in one reactor in which the multiple stages are achieved by means of appropriate internals.

The hydrogen peroxide can be distributed over the individual reactors depending upon the desired conversion. The hydrogen peroxide employed is commercial hydrogen peroxide having a concentration ranging from 10 to 70% of hydrogen peroxide in water.

After the reaction has ended and complete phase separation has taken place, the tungsten can be extracted from the organic phase by extraction, optionally multiple extraction, with water which may, if appropriate, contain basic additives such as sodium carbonate, sodium hydrogen carbonate or sodium hydroxide. The alkane together with residual unreacted alkene can then be removed by distillation. The pure epoxide is obtained from the bottoms from this distillation by fine distillation. The pretreatment serves to purify the product before the distillation so as to reduce the formation of by-products.

The temperature of the epoxidation reaction can range from 50 to 120° C. Preferred temperatures range from 70 to 100° C.

The epoxidation reaction is preferably conducted under a protective gas of nitrogen, argon or carbon dioxide.

Having generally described this invention, a further understanding can be obtained by reference to certain specific examples which are provided herein for purposes of illustration only and are not intended to be limiting unless otherwise specified.

EXAMPLE 1

Comparative Example

Figure 2:
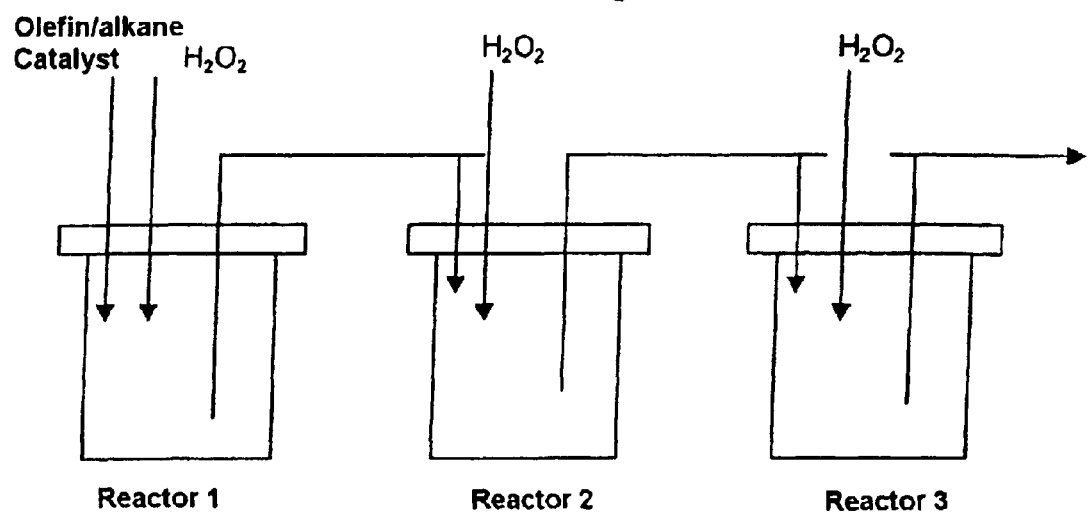
FIG. 2 illustrates an embodiment of the present invention in which the epoxidation of a olefin in the presence of a catalyst occurs in several reactors.

In an apparatus of the type depicted in FIG. 2, 249 g of cyclododecene (1.5 mol), 0.99 g of sodium tungstate, 0.59 g of phosphoric acid, 14 g of water, 1.2 g of Aliquat 336 (Cognis) and 10.2 g of hydrogen peroxide were placed in reactor 1 and brought to a pH of 3 by means of the addition of sulfuric acid. The mixture was then heated to 90° C. and 102 g of 50% strength hydrogen peroxide solution were metered in over a period of 2 hours. A cyclododecene conversion of about 90% was achieved in reactor 1. The volume was about 300 ml. From that point onward, 2.7 ml/min of a mixture of cyclododecene with 0.2 mol % of Aliquat 336 and with 0.73 ml/min of a solution comprising 0.94% of sodium tungstate, 0.56% of phosphoric acid and 98.5% of hydrogen peroxide (50% strength) were metered in continuously over a period of 4 hours. The mixture traveled continuously via an overflow to reactor 2 which likewise had a volume of 400 ml and was operated at 90° C. After four hours of continuous operation, the conversion in reactor 3 was 99.6%.

After the reaction, the settling time of the mixture in reactor 3 was determined. The settling time is the time after which the aqueous phase has settled to such an extent that the two-phase layer at the edge of the reactor was less than 1 mm. The settling time was checked every 15 seconds. The determination of the settling time was repeated twice and a mean was calculated. The results are shown in Table 1.

EXAMPLE 2

Example According to the Invention

The experiment was conducted by a method analogous to that of Example 1, except that 2% of cyclododecane based on cyclododecene was added to the starting material. The results are shown in Table 1.

EXAMPLE 3

Example According to the Invention

The experiment was conducted by a method analogous to that of Example 1, except that 5% of cyclododecane based on cyclododecene was added to the starting material. The results are shown in Table 1.

EXAMPLE 4

Example According to the Invention

The experiment was conducted by a method analogous to that of Example 1, except that 10% of cyclododecane based on cyclododecene was added to the starting material. The results are shown in Table 1.

EXAMPLE 5

Example According to the Invention

The experiment was conducted by a method analogous to that of Example 1, except that 15% of cyclododecane based on cyclododecene was added to the starting material. The results are shown in Table 1.

EXAMPLE 6

Example According to the Invention

The experiment was conducted by a method analogous to that of Example 1, except that 20% of cyclododecane based on cyclododecene was added to the starting material. The results are shown in Table 1.

EXAMPLE 7

Example According to the Invention

The experiment was conducted by a method analogous to that of Example 1, except that 25% of cyclododecane based on cyclododecene was added to the starting material.

EXAMPLE 8

Example According to the Invention

The experiment was conducted by a method analogous to that of Example 1, except that 30% of cyclododecane based on cyclododecene was added to the starting material.

TABLE 1

| Example No. | Cyclododecane content [by weight] | Settling time [seconds] |
| --- | --- | --- |
| 1 (comparison) | 0 | 300 |
| 2 | 2 | 255 |
| 3 | 5 | 200 |
| 4 | 10 | 180 |
| 5 | 15 | 160 |
| 6 | 20 | 150 |
| 7 | 25 | 135 |
| 8 | 30 | 125 |

FIG. 1 is a graph of the settling times presented in Table 1 versus cyclododecane content of the experiments of Examples 1–8. It is clear that even at 2% by weight of cyclododecane, the settling time is significantly reduced from 300 seconds to 255 seconds. In the presence of 5% by weight alkane, the settling times decreases to 200 seconds which is ⅔rds of the original settling time. Thus the present invention makes possible industrial phase separation using the phase separators of the present invention.

German priority application Serial Number 102 47 496.6 filed Oct. 11, 2002, is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A method of improving settling times of catalyst in the epoxidation of a cyclic, at least monounsaturated alkene, comprising:

epoxidizing a cyclic, at least monounsaturated alkene having from 8 to 20 carbon atoms in the ring in a reaction medium containing an oxidant and a catalyst system comprising at least one metal of Groups 4, 5 and 6 of the Periodic Table of the Elements, phosphoric acid and a phase transfer catalyst and a cyclic alkane having from 8 to 20 carbon atoms in the ring, which corresponds to the alkene reactant, as settling accelerator in the epoxidation reaction.

2. The method of claim 1, wherein the amount of cyclic alkane in the reaction medium is at least 1% by weight.

3. The method of claim 2, wherein the amount of cyclic alkane in the reaction medium is at least 2.5% by weight.

4. The method of claim 1, wherein the epoxidation reaction is conducted continuously.

5. The method of claim 1, wherein the oxidant is hydrogen peroxide.

6. The method of claim 1, wherein the reaction medium comprises at least two liquid phases.

7. The method of claim 1, wherein the pH of the reaction medium is maintained at a value in the range from 2 to 6.

8. The method of claim 7, wherein the pH of the reaction medium is maintained at a value in the range from 2.5 to 4.

9. The method of claim 1, wherein the cyclic alkane is cyclododecane and the cyclic alkene is cyclododecene.

10. The process as claimed in claim 1, wherein the reaction mixture comprises at least one phase transfer catalyst and phosphoric acid.

11. The process as claimed in claim 10, wherein the phase transfer catalyst comprises at least one tertiary amine and/or a quaternary ammonium salt.

12. The process as claimed in claim 11, wherein the wherein the quaternary ammonium salt has the formula:

$$[NR_1R_2R_3R_4]^+X^-$$

wherein $R_1$, $R_2$, $R_3$ and $R_4$ each, independently of one another, is a linear or branched, optionally substituted, alkyl chain having from 1 to 20 carbon atoms or an optionally substituted aryl group having from 6 to 10 atoms and $X^-$ is a counterion which is chloride, bromide, fluoride, iodide, hydrogensulfate, acetate, propionate or formate.

13. The process as claimed in claim 1, wherein the catalyst is molybdenum, tungsten, chromium, vanadium or titanium metal, $Mo(CO)_6$, $W(CO)_6$, $MoO_2$, $Mo_2O_5$, $Mo_2O_3$, $MoO_3$, $WO_2$, $W_2O_5$, $WO_6$, $CrO_2$, $Cr_2O_3$, $CrO_3$, $VO_2$, $V_2O_5$, $ZrO_2$, $TiO$, $TiO_2$, $Ti_2O_3$, $NbO_2$, $Nb_2O_3$, $Nb_2O_5$, $MoS_2$, $MoS_3$, $MoS_4$, $Mo_2S_3$, $Mo_2S_5$, an oxychloride of molybdenum, tungsten, chromium, vanadium, zirconium, titanium; a fluoride, chloride, bromide, iodide, nitrate, sulfate, phosphate, pyrophosphates polyphosphate, borate, carbonate, formate, octanoate, dodecanoate, naphthenate, stearate, oxalate, succinate, glutarate, adipate, benzoate, phthalate or a benzenesulfonate of molybdenum, tungsten, titanium, chromium, zirconium or vanadium; an acetylacetonate or phthalocyanine complex of molybdenum, tungsten, chromium, vanadium or titanium; molybdic, tungstic, vanadic or chromic acid; phosphomolybdic, phosphotungstic, arsenomolybdic or arsenotungstic acid or the alkali metal or alkaline earth metal salts of these acids.

14. The method of claim 1, wherein the cyclic alkene reactant is cyclooctene, cyclooctadiene, cyclodecene, cyclododecene, cyclododecadiene, cyclododecatriene or dicyclopentadiene.

15. The method of claim 1, wherein the temperature of the reaction ranges from 50 to 120° C.

16. The method of claim 15, wherein the temperature of the reaction ranges from 70 to 100° C.

17. The method of claim 1, wherein the epoxidation reaction is conducted in a cascade of 2 to 8 reactors.

* * * * *